United States Patent [19]

Wurtman et al.

[11] Patent Number: 4,971,998

[45] Date of Patent: Nov. 20, 1990

[54] METHODS FOR TREATING THE PREMENSTRUAL OR LATE LUTEAL PHASE SYNDROME

[75] Inventors: Richard J. Wurtman; Judith J. Wurtman, both of Boston, Mass.

[73] Assignee: Massachusetts Institute of Technology, Cambridge, Mass.

[21] Appl. No.: 244,944

[22] Filed: Sep. 15, 1988

Related U.S. Application Data

[63] Continuation-in-part of Ser. No. 111,711, Oct. 22, 1987.

[51] Int. Cl.$^5$ .................................... A61K 31/135
[52] U.S. Cl. ................................................ 514/654
[58] Field of Search ...................................... 514/654

[56] References Cited

U.S. PATENT DOCUMENTS

| | | | |
|---|---|---|---|
| 4,018,895 | 9/1977 | Molloy et al. | 514/564 |
| 4,210,637 | 1/1980 | Wurtman et al. | 514/564 |
| 4,309,445 | 1/1982 | Surtman et al. | 514/564 |
| 4,314,081 | 5/1982 | Molloy et al. | 514/564 |
| 4,452,815 | 5/1984 | Wurtman et al. | 514/564 |
| 4,590,213 | 5/1986 | Stark | 514/564 |
| 4,649,161 | 10/1987 | Wurtman et al. | 514/564 |

FOREIGN PATENT DOCUMENTS

| | | |
|---|---|---|
| 0123469 | 10/1984 | European Pat. Off. . |
| 0253146 | 6/1987 | European Pat. Off. . |
| 2129299A | 6/1982 | United Kingdom . |

OTHER PUBLICATIONS

Wurtman, J. et al., *International Journal of Eating Disorders*, vol. 4, No. 1, 789-99 (1985).
O'Rourke, D. et al., *In: Annals of the New York Academy of Sciences*, Wurtman, R. J. and J. J. Wurtman (Ed.) 449:329-330 (1987).
Lieberman, H. R. et al., *American Journal of Clinical Nutrition*, 44:772-778 (1986).
D. R. Rubinow and P. Roy-Byrne, *The American Journal of Psychiatry*, 141:163-172 (1984).
P. M. S. O'Brien, *Drugs*, 24:140-151 (1982).
A. J. Rapkin et al., *Obstetrics and Gynecology*, 70(4):533-537 (1987).
J. J. Wurtman, *Journal of Clinical Psychiatry*, 49(8):37-39 (1988).
Vaatstra, W. J. et al., *Eur. J. Pharmacol.*, 70:195-202 (1981).
Waldmeier, P. C. et al., *Eur. J. Pharmacol.*, 46:387-391 (1977).
Waldmeier, P. C. and Delini-Stula, A. A., *Eur. J. Pharmacol.*, 55:363-373 (1979).
Waldmeier, P. C. *Eur. J. Pharmacol.*, 60:315-322 (1979).
Diggory, G. L. et al., *Arch. Int. Pharmacodynam.*, 248:86-104 (1980).
James, T. A. and Starr, M. S., *J. Pharm. Pharmacol.*, 32:196-200 (1980).
Blundell, J. E. and Latham, J. C., *In: Central Mechanism of Anoretic Drugs*, S. Garattini and R. Samanin, Eds., pp. 83-109, Raven Press, NY (1977).
Samanin, R. et al., *Prog. Neuro-Psychopharmacol.*, 4:363-369 (1980).
Benfield, P. et al., *Drugs*, 32(6):481-508 (1986).
Moses, P. L. and Wurtman, R. J., *Life Sciences*, 35:1297-1300 (1984).
Kim, S. and Wurtman, R. J., *Physiology & Behavior*, 42:319-322 (1977).

*Primary Examiner*—Stanley J. Friedman
*Attorney, Agent, or Firm*—Hamilton, Brook, Smith & Reynolds

[57] ABSTRACT

Compositions useful in the treatment of disturbances of appetite, disturbances of mood, or both, associated with premenstrual syndrome, as well as methods of use therefor. The compositions include serotoninergic drugs, such as d-fenfluramine and fluoxetine.

4 Claims, No Drawings

METHODS FOR TREATING THE PREMENSTRUAL OR LATE LUTEAL PHASE SYNDROME

DESCRIPTION

1. Related Application

This application is a continuation-in-part of U.S. patent application Ser. No. 111,771, filed Oct. 22, 1987.

2. Background

Each month, for a few days prior to the onset of menstruation, many millions of otherwise-healthy American women develop symptoms of disturbed mood and appetite that can be strikingly similar to those reported by patients with Seasonal Affective Disorder (SAD), carbohydrate-craving obesity, or the non-anorexic variants of bulimia. This syndrome was first termed "premenstrual tension" by R. T. Frank in 1931 and is a very common phenomenon. According to Guy Abraham of UCLA, ". . . of every ten patients to walk into a gynecologist's office, three or four will suffer from premenstrual tension . . . ", and in some the symptoms will be of such severity as to include attempts at suicide. *Current Progress in Obstetrics and Gynecology*, 3:5–39 (1980).

Initial descriptions of the Premenstrual Syndrome (PMS) focused on its association with "nervous tension", headache, and weight gain. The weight gain observed was initially attributed to excessive retention of salt and water, which does indeed occur in some PMS patients. However, it soon became evident that it was also a consequence of the widespread tendency of PMS individuals to crave and overconsume carbohydrates, particularly foods with a sweet taste. PMS is also now referred to as late luteal phase syndrome. D.N.S. III, Revised, American Psychiatric Association (1987).

There have been numerous suggestions made about the etiology of PMS. For example, some hypothesized that it was caused by a uterine toxin. Others suggested its cause was overconsumption of sweets, which was presumably followed by excessive insulin secretion, hypoglycemia, and inadequate brain glucose and resulted in the often observed depression and anxiety. It has also been postulated that the behavioral symptoms result from the tissue edema often observed and that the psychological changes result from feelings of loss or the social complexities generated by the discomforts of menstruation.

However, none of these theories has been substantiated: PMS can persist after hysterectomy and, hence, uterine toxins cannot be its cause; the hyperinsulinism of PMS is not associated with low blood glucose levels, and is probably the consequence of a behavioral aberration (i.e., the tendency of premenstrual women to choose high-carbohydrate diets, which potentiate insulin secretion) ——rather than the cause; the mood and appetitive changes of PMS are poorly correlated with the tissue swelling; and subhuman primates who are presumably exempt from the psychodynamic or social complexities of human life, also exhibit characteristic behavioral changes premenstrually.

There have been many treatments suggested for overcoming or reducing the symptoms of PMS. These include carbohydrate-free diets, vitamin supplements, ovarian hormones, detoxifying agents, irradiation of the ovaries and pituitary, and use of diuretics. These approaches have all had limited success, however, and a means of treating the mood and appetite disturbances commonly experienced on a recurring basis by a large number of women would be of great benefit.

SUMMARY OF THE INVENTION

The present invention is based on the discovery that administration of an agent which selectively enhances serotonin-mediated neurotransmission is useful in the treatment of disturbances of mood (e.g., depression, anxiety) and of appetite (e.g., carbohydrate craving, weight gain) commonly associated with the Premenstrual Syndrome (PMS). Agents or drugs useful in enhancing serotonin-mediated neurotransmission, or the effect of serotonin within the brain synapses, are referred to as serotoninergic drugs and include (1) drugs which act to increase the quantity of serotonin present within the synapses and (2) drugs which act to enhance the effects of serotonin present with brain synapses, generally by activating post-synaptic serotonin receptors.

Drugs which act to increase the quantity of serotonin within brain synapses include those which act to increase serotonin production, cause its release, or suppress its reuptake; those which block presynaptic receptors; and those which block the activity of monoamine oxidase. Related drugs, the serotonin agonists, share with these drugs the ability to enhance serotonin-mediated neurotransmission.

One or more of these serotoninergic drugs can be administered to an individual in an amount effective to reduce or prevent the mood and/or appetite disturbances which would otherwise be observed in the individual prior to onset of menstruation. The drug (or drugs) can be administered, for example, orally, by subcutaneous, or other injection, intravenously, parenterally, transdermally, or rectally and can be given in various forms, such as a powder, tablet, capsule, solution or emulsion. In these various forms, the serotoninergic drug or drugs can be combined with additional substances, such as those needed to serve as fillers, diluents, binders, flavorings or coloring agents or coating materials.

The length of time during which a serotoninergic drug or drugs will be given varies on an individual basis, but will generally begin 1 to 14 days prior to menstruation and may continue for several days (e.g., 3 days) after onset of menstruation.

In one embodiment of the present invention, d-fenfluramine, or d,1-fenfluramine, which act to release serotonin and inhibit its inactivation by reuptake, is administered to an individual, prior to the onset of her menstrual period, in a quantity sufficient to ameliorate or prevent the mood disturbances and/or to suppress the weight gain and the increased appetite which otherwise would be evident. In a further embodiment, fluoxetine, which acts to inhibit reuptake of serotonin, is administered in a quantity sufficient to suppress these effects.

Administration of a serotoninergic drug according to the method of the present invention is of great benefit to women who experience disturbances of mood and/or appetite prior to onset of their menstrual period because the drug or drugs administered act to alleviate or prevent such adverse premenstrual symptoms.

DETAILED DESCRIPTION OF THE INVENTION

The present invention relates to compositions useful in alleviating or preventing disturbances of mood and/or appetite which occur prior to onset of menstruation, as well as to methods of their use in treating such disturbances. Such compositions include one or more serotoninergic agents or drugs (i.e., one or more agents or drugs which selectively enhance serotonin-mediated neurotransmission).

Serotoninergic drugs included in compositions of the present invention act to enhance serotonin-mediated neurotransmission by increasing the quantity of serotonin present within brain synapses, by activating post-synaptic serotonin receptors, or both. One or more of such serotoninergic drugs may be present in a composition of the present invention and may be present alone (i.e., only serotoninergic drug(s)) or in combination with other substances which function in another capacity (e.g., as a filler, binder, etc.), as described below.

The neurotransmitter serotonin (5-hydroxytryptamine or 5-HT) is 3-(beta-aminoethyl)-5-hydroxyindole. It stimulates or inhibits a variety of smooth muscles and nerves and, among others, has effects on secretion by both exocrine and endocrine glands and on functioning of the respiratory, cardiovascular and central nervous systems. Within the central nervous system (CNS), serotonin serves as a neurotransmitter in the brain and spinal cord, where it is the chemical transmitter of neurons referred to as tryptaminergic or serotoninergic neurons. These neurons are involved in control of sleep, appetite, nutrient selection, blood pressure, mood, endocrine secretion, aggressivity and numerous other sensitivities to external stimuli.

Numerous substances or drugs have been shown to affect serotonin activity. For example, endogenous serotonin levels can be increased by administering tryptophan, the precursor of serotonin. Fernstrom, J. D. and Wurtman, R. J., *Science*, 173:149–152 (1971).

It has now been discovered that administration of an agent or a drug which selectively enhances serotonin-mediated neurotransmission suppresses the weight gain and the increased appetite, particularly for carbohydrates, as well as decreasing the depression and other negative mood states, which many women experience prior to onset of menstruation. An agent or a drug which selectively enhances serotonin-mediated neurotransmission has been shown to be particularly effective in having these effects.

Administration of a drug (or drugs) which enhances serotonin-mediated neurotransmission by increasing the quantity of serotonin within brain synapses or by activating post-synaptic serotonin receptors results in amelioration or elimination of these commonly-experienced adverse effects.

For example, it has been shown that administration of d-fenfluramine (an anorectic drug) to women prior to onset of their menstrual period results in a decrease in depression and other negative mood states (e.g., tension, anger, confusion, irritability), as assessed using recognized tests (see Example 1) and in lower consumption of high-carbohydrate foods than observed when they were not given the drug (i.e., were given a placebo). A d-fenfluramine analogue, d,1-fenfluramine, has the same effect.

Similarly, administration of fluoxetine, which suppresses reuptake of serotonin and, thus, increases the quantity of serotonin available at brain synapses, has been shown to ameliorate the depressed moods and carbohydrate craving otherwise seen in subjects prior to their menstrual period. In addition, it was effective in suppressing the weight gain usually associated with the premenstrual phase in the subjects studied.

In place of, or in addition to, d-fenfluramine, d,1-fenfluramine and fluoxetine, other drugs which have the effect of enhancing serotonin-mediated neurotransmission can be administered. For example, the quantity of serotonin present at a given time or over a period of time can be enhanced by administering a drug which has any of the following effects:

1. increases serotonin production (e.g., tryptophan lithium);
2. causes serotonin release, e.g., d-fenfluramine, d,1-fenfluramine chlorimipramine (also known as clomipromine);
3. suppresses serotonin reuptake, e.g., fluoxetine, fluvoxamine, citalopram, femoxetine, cianopramine, ORG 6582, RU 25591, LM5008, sertraline or 1S-4S-N-methyl-4-(3,4 dichlorophenyl)-1,2,3,4,-tetrahydro-1-naphthylamine, paroxetine, DU 24565, indalpine, CGP 6085/A, WY 25093, alaprociate, zimelidine, cyanimipramine, desyrel (trazodone hydrochloride) or trazodone amitriptyline or elavil (amitriptyline hydrochloride), imipramine or tofranil (imipramine hydrochloride), trimipramine or surmontil, doxepin or sinequan (doxepin hydrochloride), protriptyline or vivactil (protriptyline hydrochloride), nortriptyline or aventyl (nortriptyline hydrochloride), dibenzoxazepine (also known as amoxapine or asendin);
4. blocks presynaptic receptors, e.g., metergoline, methysergide, cyproheptadine (which can also block postsynaptic receptors); or
5. blocks monoamine oxidase, e.g., deprenyl, marplan or isocarboazide, nardil (phenelzine sulfate) or phenelzine, parnate (tranylcypromine sulfate) or tranylcypromine, furazolidone, procarbazine, moclobemide or aurorix, brofaromine). The chemical names of DU 24565, CGP 6085/A, and WY 25093 are, respectively, 6-nitroquipazine, 4-(5,6-dimethyl-2-benzofuranyl) piperidine HCl, and 1-[1-([indol-3-yl]methyl) piperid-4-yl]-3-benzoylurea, respectively. Classen, K., et al., *Naunyn Schmiedebergs Arch. Pharmacol.*, 326(3): 198–202 (1984); Kulakowski, E.C. *et al.*, *Clin. Exp. Hypertens.* [A], 7(4): 585–604 (1985); Diggory, G.L. *et al.*, *Arch. Int. Pharacodyn. Ther.*, 248(1): 86–104 (1980).

Alternatively, serotonin-mediated neurotransmission can be enhanced by administering a drug, such as quipazine, m-CPP, MK212 or CM57493, which activates post-synaptic serotonin receptors.

In either case, such agents or drugs can be administered individually or in combination. The quantity of an individual drug to be administered will be determined on an individual basis and will be based at least in part on consideration of the individual's size, the severity of symptoms to be treated and the result sought.

The agent(s) or drug(s) can be administered orally, by subcutaneous or other injection, intravenously, parenterally, transdermally, or rectally. The form in which the drug will be administered (e.g., powder, tablet, capsule, solution, emulsion) will depend on the route by which it is administered.

The composition of the present invention can optionally include, in addition to the serotoninergic drug or drugs, other components. The components included in a particular composition are determined primarily by the manner in which the composition is to be administered. For example, a composition to be administered orally in tablet form can include, in addition to one or more serotoninergic drugs, a filler (e.g., lactose), a binder (e.g., carboxymethyl-cellulose, gum arabic, gelatin), an adjuvant, a flavoring agent, a coloring agent and a coating material (e.g., wax or a plasticizer). A composition to be administered orally, but in liquid form, can include one or more serotoninergic drugs, and, optionally, an emulsifying agent, a flavoring agent and/or a coloring agent.

In general, the composition of the present invention is administered to an individual prior to the expected onset of her menstrual period. The length of time during which the drug (or drugs) is administered varies on an individual basis, but in general will be from 1 to 14 days prior to onset of menstruation and might continue (e.g., 3 days) after its onset. The dose of serotoninergic drug administered daily will also vary on an individual basis and to some extent will be determined by the type and severity of symptoms to be treated. If the serotoninergic drug administered is d-fenfluramine or d,1-fenfluramine, a dose of from approximately 7 mg/day to approximately 60 mg/day is administered. As described in Example I, a dose of 30 mg/day of d-fenfluramine has been shown to be effective in decreasing depression and other negative mood states in subjects. In the case of fluoxetine administration, a dose of from approximately 5 mg/day to approximately 120 mg/day is administered. As described in Example II, a dose of 40 mg/day, given on alternate days, has been shown to be effective in ameliorating the depressed mood and carbohydrate craving reported by subjects not given fluoxetine. It was also effective in suppressing the weight gain usually experienced. (See Example II). The serotoninergic drug can be administered in a single dose or in a number of smaller doses over a period of time; for example, the 30 mg/day dose of d-fenfluramine can be administered in a series of smaller doses over the course of the day.

The present invention will now be illustrated by the following examples, which are not to be taken as limiting in any way.

EXAMPLE I

Assessment of effect of d-fenfluramine on Mood and Appetite Disturbances Associated with PMS Seventeen women received either d-fenfluramine (30 mg/day) or a placebo for 15 days prior to their expected menstrual period. Each subject participated in 6 randomized test periods; in 3 of the test periods, each was given d-fenfluramine and in the other 3 test periods, was given a placebo. Mood was assessed 1–3 days before the onset of menses, using the Hamilton Depression Scale and the PMS Symptom Rating Scale, for mood and appetite symptoms. Hamilton, N., *Journal of Neurosurgery and Psychiatry*, 23:56–62 (1960); Steiner, M. *et al.*, *Acta Psychiatrica Scandinavia*, 62:177–190 (1980). Food intake was measured through the use of self-reports (when subjects were out-patients), and directly (while subjects were inpatients), during one drug and one placebo period; subjects also were weighed. As shown in Table 1, 15 of the 17 patients reported a decrease in depression and other negative mood states (such as tension, anger, confusion, and irritability) following drug treatment, but not following placebo treatment.

TABLE 1

Effect of D-fenfluramine on PMS Symptoms of Mood (Hamilton Depression Scale*)

| Patient No. | Placebo | D-fenfluramine |
|---|---|---|
| 1 | 7 | 1 |
| 2 | 11 | 2 |
| 3 | 12 | 2 |
| 4 | 10 | 14 |
| 5 | 12 | 20 |
| 6 | 14 | 6 |
| 7 | 14 | 9 |
| 8 | 17 | 10 |
| 9 | 17 | 9 |
| 10 | 18 | 15 |
| 11 | 18 | 0 |
| 12 | 21 | 4 |
| 13 | 22 | 5 |
| 14 | 23 | 6 |
| 15 | 26 | 15 |
| 16 | 27 | 12 |
| 17 | 29 | 1 |
| Mean Score: | 18 | 8 |

*Higher scores on these tests indicate greater severity of symptoms.

It was found that consumption of high carbohydrate foods increased for patients taking the placebo, but not for patients treated with d-fenfluramine. Appetite and mood (measured by the "PMS Symptoms Checklist" described by Steiner et al., ibid.) were assessed 1–3 days before the onset of menses. The results are shown in Table 2, which reflect mean scores for eleven of the seventeen women tested:

TABLE 2

Effect of D-fenfluramine on PMS Symptoms of Mood and Appetite

| Mood Scores (mean score) | Placebo | D-fenfluramine |
|---|---|---|
| PMS Sympt. Checklist | | |
| Mood | 38 | 0 |
| Appetite | 8 | 1 |
| Food Intake | | |
| Calories | 3300 | 1660 |
| CHO(g)* | 232 | 130 |
| Protein | 78 | 85 |

(Higher scores on these tests indicate greater severity of symptoms)
*CHO = carbohydrates

EXAMPLE II

Assessment of Effect of Fluoxetine on Mood and Appetite Disturbance Associated with PMS Fluoxetine (40 mg/day) was given on alternate days, starting two weeks prior to the expected onset of a subject's menstrual period. Amelioration of the depressed mood and the carbohydrate cravings was reported (using the PMS Symptom Rating Scale): Mean scores for subjects taking the placebo were 36 and 10 (for mood and appetite, respectively), and 9 and 3 for subjects taking fluoxetine. Fluoxetine also suppressed the usual weight gain associated with the premenstrual phase in these particular subjects.

EQUIVALENTS

Those skilled in the art will recognize, or be able to ascertain using no more than routine experimentation, many equivalents to the specific embodiments of the invention described specifically herein. Such equivalents are intended to be encompassed in the scope of the following claims.

What is claimed is:

1. A method for treating disturbances of mood, disturbances of appetite, or both, associated with premenstrual syndrome, comprising administering to a woman prior to onset of her menstrual period approximately 7 mg to approximately 60 mg per day of d-fenfluramine or or d, 1-fenfluramine.

2. A method for treating disturbances of mood, disturbances of appetite, or both, associated with pre-menstrual syndrome, comprising administering to a woman prior to the onset of her menstrual period, a composition consisting essentially of approximately 5 mg to approximately 120 mg of fluoxetine.

3. A method of treating depressed mood, carbohydrate craving or both associated with premenstrual syndrome, comprising administering to a woman, prior to onset of her menstrual period and on alternate days, from approximately 5 mg to approximately 120 mg of fluoxetine.

4. A method for treating negative mood states associated with premenstrual syndrome, comprising administering daily to a woman, prior to onset of her menstrual period, approximately 7 mg to approximately 60 mg of d-fenfluramine or d, 1-fenfluramine.

* * * * *

UNITED STATES PATENT AND TRADEMARK OFFICE
CERTIFICATE OF CORRECTION

PATENT NO. : 4,971,998
DATED : November 20, 1990
INVENTOR(S) : Richard J. Wurtman and Judith J. Wurtman It is certified that error appears in the above-identified patent and that said Letters Patent is hereby corrected as shown below:

In Column 1, after the Related Application section and immediately before the Background section, insert the following:

--GOVERNMENT SUPPORT
This invention was made with Government support under Grant Number NIH-5M01-RR00088 awarded by the National Institutes of Health. The Government has certain rights in the invention.--

Signed and Sealed this

Tenth Day of April, 2001

*Attest:*

NICHOLAS P. GODICI

*Attesting Officer*   *Acting Director of the United States Patent and Trademark Office*